(12) United States Patent
Cosman et al.

(10) Patent No.: US 6,259,943 B1
(45) Date of Patent: Jul. 10, 2001

(54) FRAMELESS TO FRAME-BASED REGISTRATION SYSTEM

(75) Inventors: Eric R. Cosman, Belmont; Michael A. Cundari, Hingham; Robert J. Ledoux, Bedford; Robert A. Daniels, Haverhill; Christophe P. Mauge, Somerville; Jeffrey Labuz, Brookline, all of MA (US)

(73) Assignee: Sherwood Services AG, Schaffhausen (CH)

( * ) Notice: Subject to any disclaimer, the term of this patent is extended or adjusted under 35 U.S.C. 154(b) by 0 days.

(21) Appl. No.: 09/495,623

(22) Filed: Feb. 1, 2000

Related U.S. Application Data (63) Continuation of application No. 08/885,926, filed on Jun. 30, 1997, now abandoned, which is a continuation of application No. 08/695,662, filed on Aug. 8, 1996, now abandoned, which is a continuation of application No. 08/388,758, filed on Feb. 16, 1995, now abandoned.

(51) Int. Cl.[7] .................................................... A61B 5/00
(52) U.S. Cl. ......................... 600/429; 600/417; 606/130
(58) Field of Search .................................... 600/429, 417, 600/426, 414; 606/130; 378/205, 206

(56) References Cited

U.S. PATENT DOCUMENTS

| | | | |
|---|---|---|---|
| 5,387,220 | * | 2/1995 | Pisharodi . |
| 5,389,101 | * | 2/1995 | Heilbrun et al. . |
| 5,588,430 | * | 12/1996 | Bova et al. . |
| 5,622,170 | * | 4/1997 | Schulz . |
| 5,662,111 | * | 9/1997 | Cosman . |
| 5,848,967 | * | 12/1998 | Cosman .............................. 600/426 |
| 6,006,126 | * | 12/1999 | Cosman .............................. 600/426 |
| 6,167,295 | * | 12/2000 | Cosman .............................. 600/426 |

* cited by examiner

*Primary Examiner*—Marvin M. Lateef
*Assistant Examiner*—Shawna J. Shaw (57) ABSTRACT

This invention involves apparatus and methods for relating image scan data of a patient's anatomy from an imaging scanner to a device attached to said patient's anatomy or to an apparatus located nearby said patient's anatomy. In one embodiment it includes identification of fiducial points or markers on or near the patient's anatomy in the image scan data, and subsequently relating these fiducial points to reference points or structures connected to an apparatus attached to or nearby the patient's body. Such an apparatus might be a surgical head clamp or stereotactic frame or arc which has been attached to the patient's head at the time of surgery. A mapping is made between the coordinate frame data of the scan image to the coordinate reference frame of the patient attachment means or external apparatus by physically referencing the fiducial points to the patient attachment means or external apparatus. In one embodiment, such registration can be in the form of distance or coordinate measurements between the fiducial points on the patient's body and the reference points on the external apparatus. Applications are given in the field of frameless stereotaxy, radiosurgery, and stereotactic frame application.

7 Claims, 4 Drawing Sheets

FIG_1

FIG_2

FIG_3

FIG_4

FIG_6

FIG_7

FIG_9

FRAMELESS TO FRAME-BASED REGISTRATION SYSTEM

This application is a continuation of Ser. No. 08/885,926 filed Jun. 30, 1997 now abandoned, which is a continuation of Ser. No. 08/695,662 filed Aug. 8, 1996, now abandoned, which is a continuation of Ser. No. 08/388,758 filed Feb. 16, 1995, now abandoned.

BACKGROUND TO THE INVENTION

The field of "frame-based" stereotaxy is now well established. In that field, typically, a head ring is affixed to the patient's head or skull, and a localizer frame with graphic reference means is attached to the head ring. The patient is then scanned in an image scanner, such as a CT scanner, and the fiducial markings in the image scan data from the graphic reference means are used to map the image scan data or the coordinate frame of that image scanner into the coordinate reference frame of the stereotactic head ring. Following that, the patient may typically go to surgery, a calculation or determination of an anatomical target seen in the image scan data is made, and a stereotactic arc system is attached to the head ring to pass a probe to the selected anatomical target. Examples of such systems are the Radionics BRW and CRW Stereotactic Systems. A significant feature of the frame-based system is that the head frame with graphic reference means is attached to the patient's head prior to image scanning. This causes some discomfort for the patient and is an added step. It would be desirable not to have to put such a head ring on the patient's head prior to the image scan.

The field of "frameless" stereotaxy has also emerged and developed strongly in the last few years. In this situation, fiducial markings may be placed on the patient's anatomy; these may be, for example, skin markers or natural anatomical landmarks such as the tip of the nose, ears, nasion, etc. The patient is scanned in the scanner, and these physical fiducial points are identified in the image scan data. Subsequently, the patient may be brought to the operating theater and a space navigator or digitized navigator, such as a surgical operating arm or an optically coupled digitized pointer, may be used to touch each of the physical fiducial points in sequence so as to calibrate the digitized navigator relative to the physical fiducial points and thereby calibrate the digital navigator to the coordinate reference frame of the image scanner, where those fiducial points have already been identified. The advantages of frameless stereotaxy are several but include the advantage that a head ring does not have to be put on the patient's head prior to the imaging. A further advantage is the interactive nature of the digital navigators so that the surgeon can point in a direction towards the head with the digitized navigator and visualize interactively the anatomy that will be achieved in that direction according to the image scan data, which can be rendered in two dimensions or three dimensions.

There are advantages to stereotactic frames because they are stable platforms for holding surgical instruments to reach targets within the brain. On the other hand, it is the case that in most cranial operations a patient is brought to the operating room and his head is clamped to the operating table by a surgical head clamp, which is essentially a ring or semi-ring that is attached firmly by screws to the patient's skull.

It is desirable, therefore, and an object of the present invention, to bridge the gap between the frame-based and the frameless worlds of stereotaxy and provide a system and method whereby a head ring or patient attachment means need not be attached to the patient's head prior to scanning, yet a registration of the stereotactic coordinate frame can be made relative to a head clamp which is placed on the patient's head at the time of surgery (after the image scanning episode).

A further object of the present invention is to provide a system which allows or enables a digital navigator or other type of registration apparatus to make a correspondence, mapping, or registration between the coordinate frame of the image scan data (and thus of the patient's anatomy which is detected in it) and the coordinate frame of a surgical head clamp or other type of body attachment means or external apparatus which may be used on or near the patient's body at the time of the surgical intervention or treatment (but not necessarily put on the patient at the time the image scan data is taken). There are other advantages and practical objectives of the present invention which will be manifest in the description and claims below.

DESCRIPTION OF THE INVENTION

Figures 1, 2, 3:
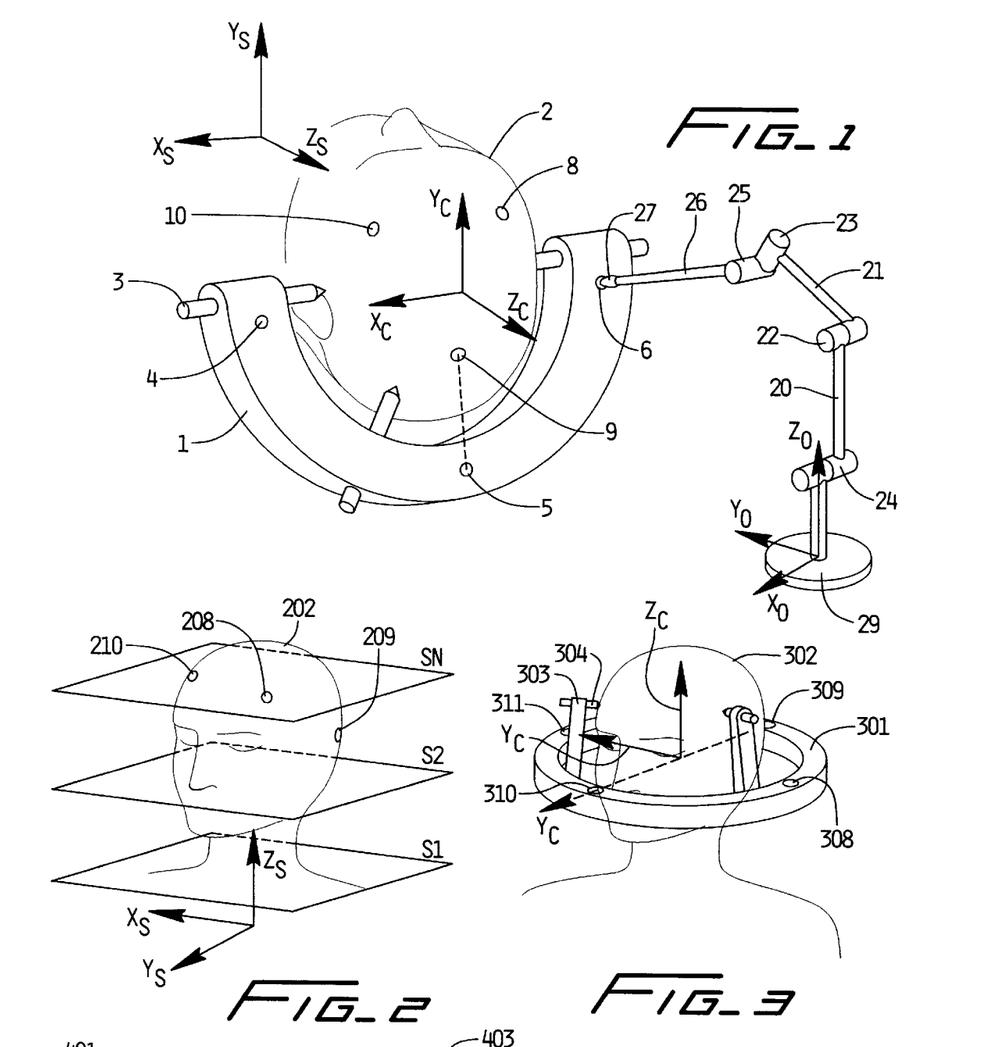
FIG. 1 shows an embodiment of the invention including a head clamp with reference points, a patient with fiducial points, and a digitized means for registering between the head clamp and the patient's coordinate systems.
FIG. 2 shows a series of image scan planes through the patient's anatomy with fiducial markers on the anatomy and a coordinate system representative of the image scanner.
FIG. 3 shows an embodiment of a head ring with its stereotactic coordinate system attached to the patient's head, with reference points on the head ring.

Referring to FIG. 1, a head clamp 1 is secured to the patient's anatomy 2 (in this case, the head) by means of a series of head screws 3. This would be a typical setting in an operating room where a surgical head clamp is applied to a patient's skull for a neurosurgical operation. As part of the embodiment of this invention, the head clamp has a series of reference points (4, 5, and 6, in this example), which are at known coordinate positions relative to a coordinate system indicated by the arrows $X_c$, $Y_c$, and $Z_c$ associated with the head clamp 1. This coordinate system can be referred to as the stereotactic coordinate system of the head clamp. Referring to FIG. 2, the patient's anatomy 22 is scanned by an image scanner such as a CT tomographic scanner which can utilize either X-rays, MRI imaging, P.E.T. imaging, etc. to produce a series of image planes represented by S1, S2, S3, ... $S_N$ through the patient's body. The scanner has a coordinate system represented by the arrows $X_s$, $Y_s$, and $Z_s$. Typically, this coordinate system would have a Z axis perpendicular to the planes of slices. The planes of the slices do not necessarily have to be parallel, but if not, other corrective actions might be taken to register the entire CT slice stack into a unified or approximately unified scanner coordinate system such as $X_s$, $Y_s$, and $Z_s$.

Also shown in FIG. 1 are fiducial points 8, 9, and 10 located on the patient's skin or near the patient's skin. These could be radiopaque or MRI-visible markers stuck onto the skin, skin staples, or they could be natural landmarks on the surface anatomy such as the tip of the nose, the ears, the nasion, etc. In FIG. 2, these fiducial markers attached to the patient's anatomy are represented as 208, 209, and 210. They may show up in one or several slices. They can be used to register the scan slice planes indicated by S1, S2, S3, . . . $S_N$, up to any number of slices to the patient's anatomy 202. Use of such fiducial markers to register the patient's anatomy, both the physical patient's anatomy and the images of said patient's anatomy, into the coordinate frame of reference of the scanner, for example the coordinate reference system $X_s$, $Y_s$, and $Z_s$, is now commonly practiced in the field of frameless stereotaxy. Such image scan data and registration to the patient's anatomy by quantitative fiducial markings which are physically located in the patient's head, and thus accessible and also visible in the scan images themselves, enable, then, a mapping of the patient's body or patient's anatomy to the CT scan coordinate space. This can be done in the scanner prior to going to surgery or for radiation therapy. Thus, the patient does not have to endure, during the scan process, the application of an invasive head clamp or any head clamp or external apparatus at all, except perhaps for relatively innocuous fiducial markers or similar markers such as 8, 9, and 10 in FIG. 1. These markers, by the way, could be substituted by a tubular or grid structure which would give similar indicia in each of the scan slices over the patient's anatomy region of interest. The fiducial markers need not be discrete points either, but rather could be contours, lines, or surfaces over the external anatomy of the patient, which can further serve to map the coordinate space of the CT scan to the patient's anatomy via identifiable physical or fiducial means relative to the patient's physical anatomy.

The fiducial marks or points 8, 9, and 10 in FIG. 1, or 208, 209, 210 of FIG. 2 can vary in number from one to many. They can be used to reference physically the physical patient's anatomy to themselves, and, by knowing the images of the fiducial marks in the image scan data from the image scan, they then enable indexing of the physical patient's anatomy space to the image data space of that anatomy from the image scanner. This concept is well known from the field of "frameless" stereo. Three fiducial points or more are typically used to establish a three-dimensional map from physical space to the image scan space, although less fiducial points could be used if it is known that all scan slices are parallel and in a specific orientation relative to the body. Typically more than three fiducial markers are used for redundancy or for increased accuracy.

FIG. 1 and FIG. 3 show the application of a head clamp or head ring in the example of the cranial localizer application. In FIG. 1, the head clamp 1, which is an open or substantially C-shaped structure, is attached to the patient's cranium by the screws, such as screw means 3. This might anchor directly to the skull or could be used non-invasively by pressure pads on the external contour, or could even be used with confirmation means to the back of the head, nasion, dental trays, etc. It then represents a patient attachment means, a head clamp, or an external apparatus, the referencing of which to the CT scan's coordinate space in the patient's anatomy is one of the objectives of the present invention. In FIG. 3, one sees a head ring 301 which is similarly attached by head posts 303 to the patient's anatomy 302 via head screws 304. The ring has reference points or reference markers 308, 309, 310, and 311 as illustrations of a placement of reference points associated with this external apparatus or head clamp. These reference markers could be, for example, divot points, or ball indents, or other physical or mechanically defined reference points that can be touched or registered to by registration means or referencing means once the head clamp has been placed on the patient's head. In FIG. 1 and FIG. 3, a coordinate system associated with the patient attachment means or the head clamp is illustrated by the coordinate arrows $X_c$, $Y_c$, and $Z_c$. For example, in the case of a head ring such as in FIG. 3, which is analogous to the head ring of the BRW/CRW Stereotactic System of Radionics, the origin of this coordinate system might be at the axial center of the ring, and the Z could be at the plane of the ring or some defined vertical level with respect to the plane of the ring. Such a choice of origin is quite arbitrary, but the coordinate reference frame, which one could refer to as the stereotactic coordinate system, associated with the patient attachment means or head clamp is in a fixed relationship to the patient attachment means, and thus represents a second coordinate reference frame in these figures as compared to the first reference frame which is associated with the scanner coordinate frame of reference or the patient's frame of reference as indicated by the $X_s$, $Y_s$, and $Z_s$ coordinate arrows.

FIG. 1 illustrates an embodiment of the present invention, including a registration apparatus 20 which is in the form of a digitized arm, the arm having links illustrated by 21 and joints illustrated by 22, 23, 24, 25, and there could be more. There is a probe on the end 26 which can point to spatial locations by means of the probe tip 27, pointing to one of the reference markers 6 which is on the head clamp 1. The registration apparatus could be termed a calibration apparatus, or a transfer apparatus, or a data mapping apparatus, or a metrology device, or some other device which enables a transformation mapping, registration, or correlation between the coordinate reference frames associated with the image scanner and/or patient's anatomy and the stereotactic coordinate reference frame associated with the patient attachment means or clamp means. To illustrate how this could work in the case of FIG. 1, the registration means is in the form of a digitized articulating arm or a digitized navigator. This is analogous to the Radionics OAS Operating Arm System (Radionics, Inc.), which gives an electronic or a digital signal for positions of the pointer 26 and the pointer tip 27 as they move in space relative to the base 29 of the operating arm. By calibrating the operating arm, the position and direction of the probe can be tracked in space and displayed on a computer graphics means (not shown in this figure). Thus, for example, the coordinate position of the tip 27 of the probe 26 could be mapped in space relative to a coordinate system of the registration apparatus, the operating arm, which is represented by the axes X, Y, and Z in FIG. 1. Thus, by touching the reference points 4, 5, and 6 on the clamp 1 in FIG. 1, the coordinate points relative to X, Y, and Z coordinate system could be measured and stored for the reference points 4, 5, and 6. Since these reference points are at known coordinate positions relative to the stereotactic coordinate system of the head clamp, $X_c$, $Y_c$, and $Z_c$, then there can be a registration or data mapping or transfer of the relationship of the stereotactic coordinate system to the coordinate system of the registration apparatus X, Y, and Z. Furthermore, the same registration apparatus could touch or be put into proximity physically to the fiducial points 8, 9, and 10, which are associated or cooperatively coupled to the patient's anatomy 2. Thus, the spatial coordinates of these fiducial points 8, 9, and 10 can be determined, measured, and stored in a computer means associated with the registration apparatus 20, and thus relative to the coordinate system X, Y, Z of the registration apparatus. If, for example, there are three or more such reference points determined on the head clamp and three or more such fiducial points on the patient's anatomy, then a data map, transformation, or otherwise registration could be made from the coordinate frame of the patient's anatomy (i.e. the scanner coordinate frame from the image scanner) to the stereotactic coordinate frame of the head clamp. This would be done by a simple transformation of coordinate systems using the definable, measurable, or predetermined coordinate positions of these respective fiducial points in the two frames just described. Although in the example of FIG. 1 the coordinates of the fiducial points and reference points are made relative to a third coordinate system X, Y, and Z of the registration apparatus, this intermediary coordinate system or third coordinate system is not necessary to do the transformation, as we will show below.

Figure 4:
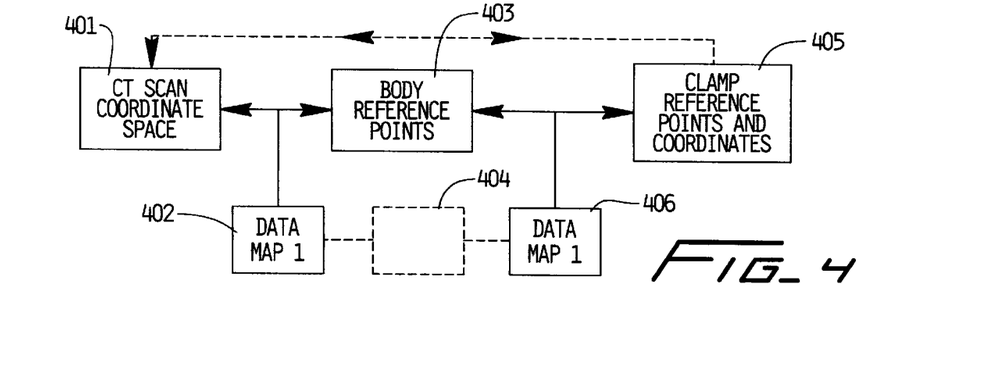
FIG. 4 is a schematic diagram showing the mapping or registration from the image scanner coordinate space to the stereotactic coordinate space of the head clamp by means of intermediate registration of the clamp reference points to the body reference points and the further registration of the body reference points to the scan coordinate space.

FIG. 4 shows, then, a schematic diagram for this particular embodiment of FIGS. 1, 2, and 3 of how a transformation or mapping between the CT scan coordinate space $X_s$, $Y_s$, and $Z_s$ can be made to the coordinate space of the stereotactic coordinate system $X_c$, $Y_c$ and $Z_c$. The coordinate scan space is represented by 401, and there is a data map or transformation between it and the patient's anatomy by means of the data mapping means 402 to the fiducial points 403, as described above. This supplies the connection between the patient's anatomy and the data points seen on the image scan slices or data from the image scanner, i.e. the coordinate frame of the scanner 401. This registration data or correlation data can be stored on a computer 404 and can be manipulated therein and displayed therein graphically on a CRT type display, as is common practice for frameless stereotaxy. Data map 1, indicated by 402, can take the form, as in FIG. 1, of using a digitized navigator, such as the OAS Operating Arm of Radionics, to touch off the fiducial points such as 8, 9, and 10 associated with the patient's body so that there is a physical correlation between these physical fiducial points to the images of these fiducial points as seen in the CT scan coordinate space of the image scanner space 401. Thus, included in this example is a registration of the physical space of the patient's anatomy to the image space or coordinate space of the scanner. Also shown in FIG. 4 is the coordinate space 405 associated with the patient attachment means or head clamp. Data map 2, illustrated by element 406, corresponds or includes the registration, mapping, and/or transformation between the fiducial points on the body, such as 8, 9, and 10 on the body in FIG. 1, and the stereotactic coordinate frame of the head clamp, such as 1 in FIG. 1, via, for example, reference points on the head clamp, such as 4, 5, and 6. Again, this data can be stored or transferred to the computer 404. The computer can, therefore, do the transformation between the image scanner and/or patient anatomy-based frame of reference (viz; ($X_s$, $Y_s$, $Z_s$)) and the frame of reference associated with the head clamp (viz; ($X_c$, $Y_c$ $Z_c$)).

The example of FIGS. 1, 2, 3, and 4 is just one of several possible means of establishing a mapping between the "frameless" space of the scanner $X_s$, $Y_s$, $Z_s$, which is registered to the anatomy by the fiducial points 8, 9, and 10, as illustrated in FIG. 1 to the coordinate space $X_c$, $Y_c$ and $Z_c$ of the head clamp 1 (designated as the stereotactic coordinate space). In this example, the mapping between the two spaces is mediated by a referencing or mapping instrument illustrated by the digital navigator 20, shown in FIG. 1. It has its coordinate space $X_0$, $Y_0$, $Z_0$, which enables the calibration, registration, and/or mapping, as described above.

Figure 5:
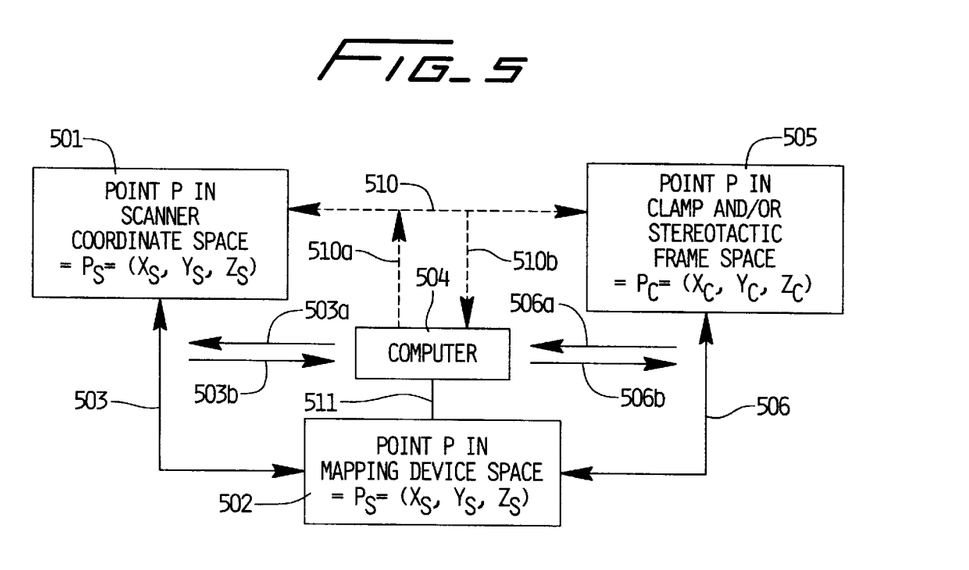
FIG. 5 shows an embodiment in which the data map between clamp space and body reference points is done by a series of distance measurements.

FIG. 5 illustrates schematically how this mapping may be designated in the particular example of FIGS. 1, 2, 3, and 4. In the upper left of FIG. 5 is the box 501, which specifies a physical point P in space, which may be identified in the image scan data or image scanner coordinate space, and that point P can be designated by the coordinates ($X_s$, $Y_s$, $Z_s$), which triplet of numbers is designated as $P_s$. It is notable that frequently the coordinate space of the image scanner is represented by the nomenclature X, Y, S, where X and Y represent the X and Y coordinates in the two-dimensional plane slice, and S represents the slice depth or the distance in the direction orthogonal to the plane slices. This can be easily calculated by looking at the slice number times the distance between slices, or some other paradigm quite common to CT or MR scan technology. In FIG. 5, the same physical point P is represented in the coordinate space of the digitizer or transfer device as ($X_0$, $Y_0$, $Z_0$), which triplet is designated by the symbol $p_0$. The digitizer can be calibrated to the scanner coordinate space, thus mapping $p_0$ to $p_s$, as illustrated by the arrow 503. This may be mediated by the connection 511 between the digitize device and a computer 504, and the computer can go through a calibration maneuver on the fiducial points such as 8, 9, 10 in FIG. 1, as illustrated by the line 503B, and thereafter can map any point in the digitizer space $p_0$ to the scanner space $p_s$, going backwards and forwards, as illustrated by the double arrow on the line 503. Similarly, on the upper right portion of FIG. 5, the physical point P is designated in the coordinate space of the clamp, which we refer to as the stereotactic frame space or stereotactic coordinate space by the triplet ($X_c$, $Y_c$, $Z_c$), this triplet being designated by the symbol $p_c$. Again, by a calibration maneuver, the mapping between $p_0$ space and $p_c$ space is illustrated by the line 506, and the calibration line 506B between the computer 504, coupled with the digitizer, once calibration has been complete, will enable mapping of any point $p_0$ into $p_c$ space, as illustrated by the computation line 506A between the computer and the mapping line 506. Whereafter, once the mapping between $P_0$ and $p_s$ and the mapping between $P_0$ and $p_c$ is complete and stored in the computer 504, then the computer can easily map or make transitions between $p_s$ and $p_c$ space, illustrated by the arrow 510, which can go in either direction. The computer can thus manipulate the points from $p_c$ to $p_s$ and vice versa, and the connection between the computer is illustrated as flow of data back and forth between transition and mapping by the lines 510A and 510B. To further detail this one illustrative example of the invention to indicate how the calibrations of mappings 503 and 506 may be done, we can specify that there are reference points on the head clamp which can be designated as follows:

$$(R_i)_c = (X_{ci}, Y_{ci}, Z_{ci}); i=1, 2, 3, \ldots$$

where $X_{ci}$, $Y_{ci}$, and $Z_{ci}$ represent the coordinate components of the reference point $R_i$ in the clamp coordinate frame, and index i represents the identification of each of the individual reference points (for example, the points 4, 5, and 6 in FIG. 1), i can be any number, depending on the assumption of scan parallelity, but it is convenient to have the number of reference points to be greater than three. Similarly, the fiducial points, as illustrated, for example, in FIG. 1 by the points 8, 9, and 10, can be designated as follows:

$$(F_j)_s = (X_{sj}, Y_{sj}, Z_{sj}); j=1, 2, 3, \ldots$$

where $F_j$ represents the triplet vector for the j fiducial point and its coordinates in the scanner space are indicated by the components $X_{sj}$, $Y_{sj}$, and $Z_{sj}$, where again j runs through the index points, which are conveniently greater than three in number. Each of these reference and fiducial points can have their coordinate components as in the coordinate frame of the navigator 20 in FIG. 1, as illustrated in the following equations:

$$(R_i)_o = (X_{oi}, Y_{oi}, Z_{oi}); i=1, 2, 3, \ldots$$

$$(F_j)_o = (X_{oj}, Y_{oj}, Z_{oj}); j=1, 2, 3, \ldots$$

A calibration procedure to determine the matrix transformation between the $P_0$ coordinate system and the $P_c$ coordinate system would be determined by making measurements for each of these coordinate vectors and then relating them by the coordinate equation:

$$(R_i)_c = A(R_i)_0$$

The similar calibration equation to map between the coordinate space $P_0$ and $P_s$ for the fiducial points takes the form:

$$(F_j)_s = B(F_j)_0$$

Once the calibration procedure has been done for the reference and fiducial points, then the matrices A and B, which represent the mapping between the spaces, can be established. Once that matrix has been established, then the general coordinate mapping, as illustrated by FIG. 5, takes the form:

$$(P_c) = (X_c, Y_c, Z_c) = A(X_0, Y_0, Z_0) = A P_0$$

Similarly, the equation mapping the $P_0$ space to the $P_s$ space takes the form of the equation:

$$(P_s) = (X_s, Y_s, Z_s) = B(X_0, Y_0, Z_0) = BP_0$$

Then the mapping matrix M between the c space and the s space, as illustrated by the line 510 in FIG. 5, takes the following form:

$$P_s = BA^{-1} P_c = MP_c$$

$$P_c = AB^{-1} P_s = M^{-1} P_s$$

This is an example of linear algebraic matrix transformations between Cartesian coordinate spaces, and the transformations A, B, and M would be appropriate matrices.

Figure 6:
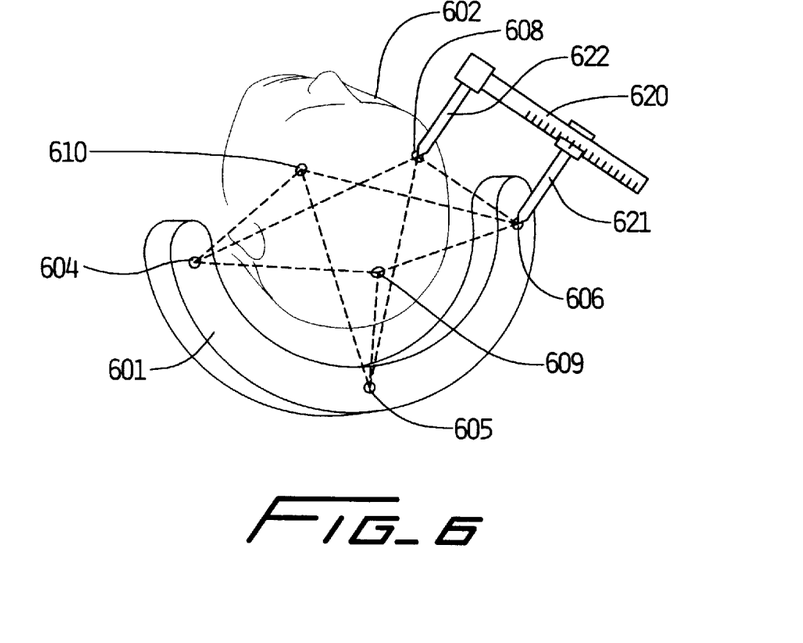
FIG. 6 shows the application of a stereotactic arc system or a stereotactic probe holder to the head clamp to set a probe path and/or a target in the clamp coordinate space.

There are other ways of making the mapping between the "frameless" space of the scanner and fiducial markers and the "frame-based" space of the head clamp and its associated reference points. One example is in FIG. 6. The head clamp is shown once again as 601, with its reference points 604, 605, and 606. It is understood that there can be more or less reference points than those illustrated in this figure. The patient's anatomy, illustrated by 602, has accordingly the fiducial points 608, 609, and 610. In this example, another type of mapping is made in a calibration procedure to transform or map the information from the image scanner space with the fiducial markings to the coordinate space of the head clamp. A simple distance micrometer, illustrated by device 620, is shown which has pointed elements or caliper-like elements 621 and 622, which, in this figure, can be set on the one end to the reference point 606 by the pointer 621, and on the other end, to the fiducial point 608 by the caliper 622. The distance designated by $D_{ij}$ represents, in this case, the linear distance, as measured by the micrometer 620, between the reference point 606 and the fiducial point 608. This distance is represented by a dashed line between 606 and 608 (not numbered). Similar dashed lines can be drawn between pairs of reference points and fiducial points, and these are shown unnumbered in FIG. 6. Thus, the symbol $D_{ij}$ represents a matrix of linear distance measurements between pairs of reference points and fiducial points;

$$D_{ij} = \text{Distance}(R_i, F_j), i, j=1, 2, 3, \ldots$$

Figure 9:
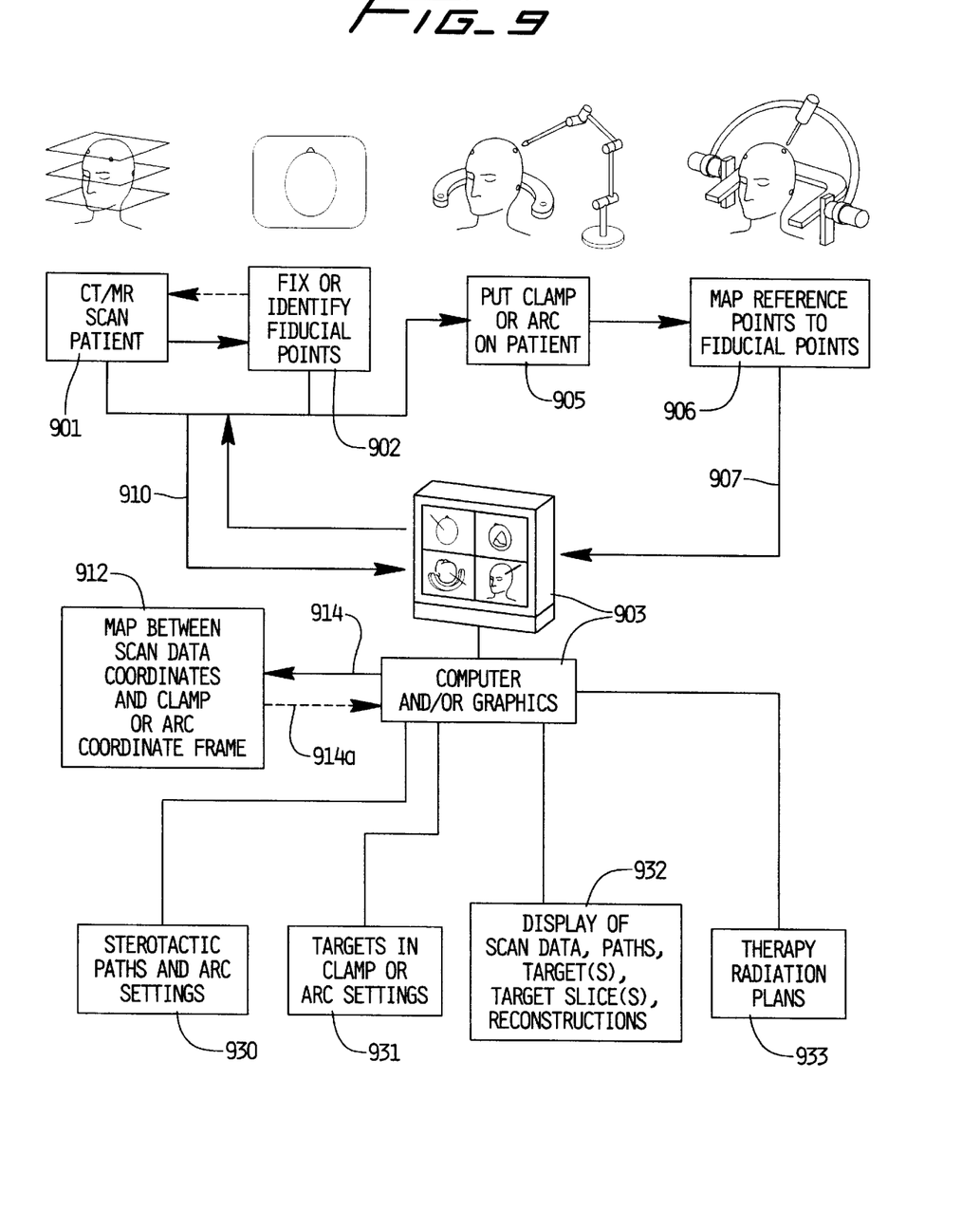
FIG. 9 shows schematically an embodiment of the present invention showing the sequence from scanning to fiducial and reference mark registration to follow-on functions.

It is a straightforward matter of analytic geometry to know that if the coordinates of the reference points $R_i$ (illustrated by 604, 605, and 606, etc.) are known in the coordinate or stereotactic space of the head clamp 601, and the coordinates of the fiducial points $F_j$ (as illustrated by 608, 609, and 610, etc.) are known in the coordinate space of the image scanner, then by measuring these linear distances, a transformation, mapping, or transformation matrix can be determined between these two coordinate spaces. Thereafter, a mapping matrix M, as illustrated in FIG. 9, can be stored in the computer and used to map uniquely from one coordinate space to the other, as illustrated in the above examples. Graphic or non-computer-based means of doing the same is possible.

Vernier caliper element 620, shown in FIG. 6, can take many forms. It can be a mechanical scale or digital linear vernier caliper which can be sterilized and brought into the operating room. It can be a compass-type caliper system where the $D_{ij}$ matrix elements are not linear distances, but rather angular distances which can be converted to the appropriate form to determine the mapping M. Other apparatus and means could be contrived by those skilled in the art to perform the same function.

Figure 7:
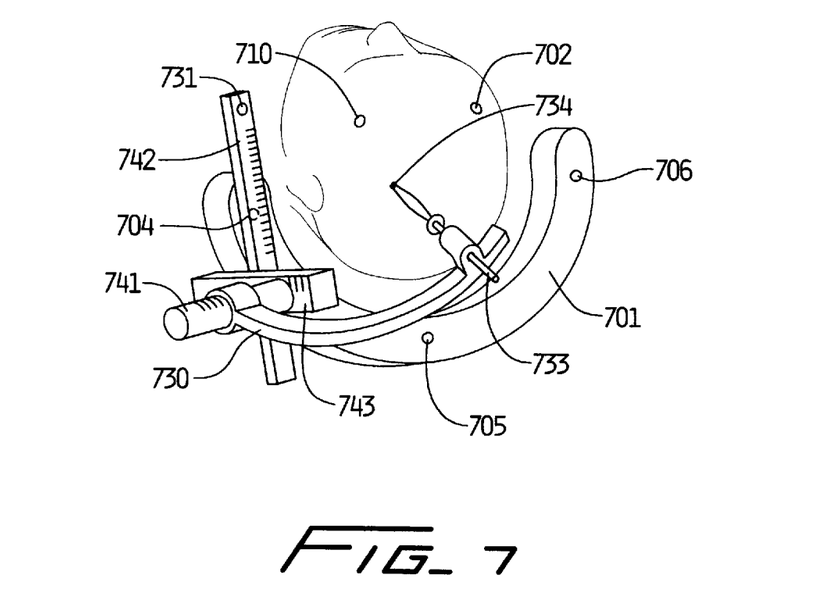
FIG. 7 shows an embodiment of the present invention related to body frameless stereotaxis together with an external treatment planning machine or external camera system for treatment and registration.

FIG. 7 shows the same frame-based head clamp 701 which can be attached to the patient's anatomy 702 by skull screws (not shown). An arc system 730 can be attached to the head clamp 701. The head clamp similarly has reference positions 704, 705, and 706, similar to those in FIGS. 1 and 6 above. The reference points could also be on the arc system itself, as indicated by 731, and there could be a multiplicity of such arc-based reference systems so that a mapping between the fiducial points illustrated by 710 on the patient, and the arc system can be done by a mapping as described above. Once such a mapping or transformation M has been determined, then the physical points P in space can be mapped between the coordinates $P_c$ of the clamp or arc system and the coordinates $P_s$ of the image scanner or patient's anatomy coordinate system. The arc can carry a treatment probe 733 that can be directed to a point 734 in the anatomy which corresponds to coordinate positions in the $P_c$ clamp or arc space. These coordinates might be the millimeter scales illustrated by 741, 742, and 743 on Cartesian or arc slides on the arc system. The arc system can be Cartesian and isocentric, as is the CRW Arc System of Radionics, Inc., or it can have angular type coordinates on non-target-centered coordinates with arc angles, as illustrated by the BRW System, also of Radionics, Inc. Thus, the registration process, illustrated by the above examples, can apply to an arc system which is placed on a head clamp and not specifically to the clamp itself. Furthermore, the mapping M between the clamp and/or arc system stereotactic space to the coordinate space of the scanner or patient can be implemented by pointing the probe 733 or the tip of the probe 734 sequentially at the fiducial points, illustrated by 710, registering those coordinate data into the computer, and thereby making the mapping M, as illustrated above. Thus, an arc system can serve in the role of the referencing, digitizing, or mapping apparatus, much in the way that the apparatus 20 in FIG. 1 and 620 in FIG. 6 serves this role.

Figure 8:
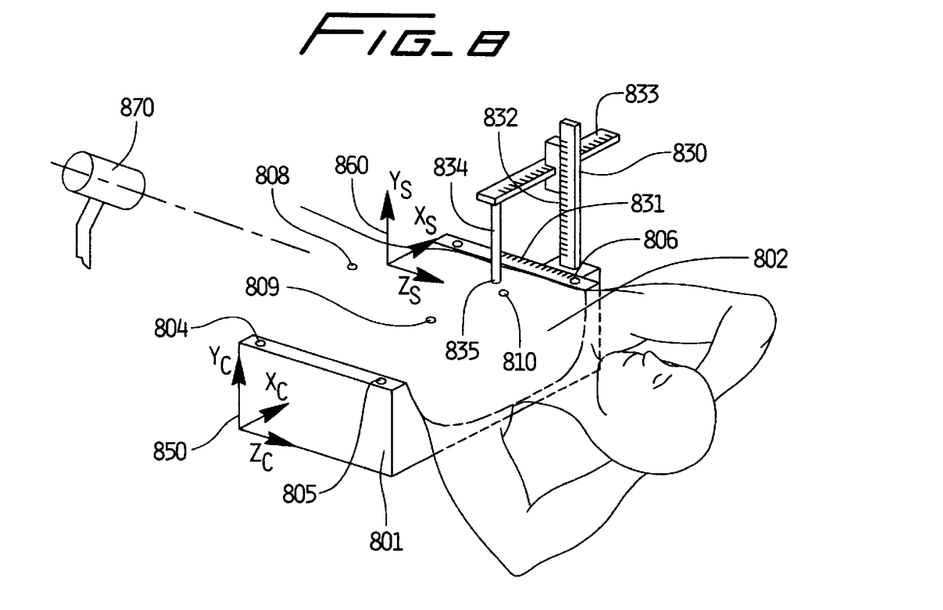
FIG. 8 shows a schematic diagram of the mapping between a measurement or registration device space and the scanner coordinate space and the stereotactic clamp or frame space so as to register the scanner space to the clamp space.

Once the mapping M has been established, arc angles for various quantitative angular approaches to a given target, as for example the approach of probe 733 in FIG. 7 to the target 734 at the tip of the probe may or may not be calculated and determined in the computer, which handles the mapping and the computer graphics from the scan itself. FIG. 8 shows yet another example of the present invention wherein the application is to targets which are not in the head, but rather elsewhere in the body. In this situation, the clamp of the above examples is replaced by a patient attachment means 801, which takes the form of a body cast or mold of, in this case, the upper torso. It has reference points illustrated by 804, 805, 806, as had the head clamp of FIG. 1. Furthermore, there are on the patient's body reference points 808, 809, and 810, which serve the same function as those on the head in the anatomy of FIG. 1. A stereotactic arc 830 is shown with Cartesian slides 831, 832, and 833, which enable a probe 834 to be translated in rectilinear coordinates in space so that its tip 835 can be set down on an index point or a fiducial point or a reference point, thereby calibrating the patient attachment means 801 to the patient's anatomy 802. A coordinate reference frame $X_c$, $Y_c$, and $Z_c$ is shown as number 850 and corresponding to the patient attachment means 801, and a body or scan reference coordinate system illustrated by the number 860 is represented by the arrows $X_s$, $Y_s$, and $Z_s$, again corresponding to the data coordinate system of the upper examples. Such an apparatus could then be used on the scanner couch during image scanning of the patient prior to placement on a radiation treatment couch. The same apparatus 801, 830, etc. could be fixedly attached or clamped or aligned to the treatment machine couch. Thus the same apparatus could provide a mapping between the couch and the radiation delivery system and the patient's anatomy and the image scan data, which is associated with the coordinate system 860. Also shown is a source of radiation delivery schematically illustrated by 870 which can deliver X-radiation or other radiation to the patient's body according to the computation of targets or target volumes within the body during a treatment planning process that could be carried out in the same computer that does the mapping, registration, and target determination from the image data relative to the stereotactic coordinate system. It might also be that the mapping can be carried out by an external apparatus such as that illustrated by 870, which could correspond to a camera pointing at the patient's body. The digitized data from the camera could be put into a computer graphic workstation and projected distances between the reference points and fiducial points made. Thus the mapping elements $D_{ij}$ corresponding to these camera measured projected distances could be accordingly determined, and the overall transformation M thereby derived. Multiple cameras could be invoked for this purpose. The cameras could, in fact, be systems of X-ray beams and X-ray imaging machines such as a C-arm or fixed single or multiple X-ray machines for this purpose, with radiopaque or other visible reference points or fiducial markers on the patient attachment means and body respectively. Thus, projected X-rays could be used to determine the mapping M in an analogous way to the mechanical or optical means discussed above.

FIG. 9 summarizes this technique of using "frameless techniques" together with a surgical head clamp or stereotactic arc system, and coordinating the two, without the need for placing the head clamp or stereotactic arc system onto the patient's head prior to scanning. This summarizes the schema illustrated in the examples and embodiments of FIGS. 1 through 8 above, but is not meant to limit the claim and scope of the invention. Box 901 and associated figure illustrate the acquisition of CT, MRI, or other scan data of the patient's anatomy, with fiducial points, natural landmarks, surface contours, etc. being using to index the anatomy to the coordinate data of the image scanner. The fiducial points can be fixed on the patient's head or identified pre- or post-scan, as illustrated by box 902. This action may interact with the scan process and can be fed into computer 903, and the computer can help by its graphics capabilities to actually make the identification or implement the fiducial means determination. Fiducial structures other than dots or points could be used and could include linear structures with diagonals attached to the patient's head so as to regularize the stack of scan data, taking into account patient movement, skewed scans, etc. This scanning and fiducial registration with the computer would be done prior to the patient going to the operating room. Subsequently, upon going to the operating or treatment room, box 905 in FIG. 9 with the associated figure shows that the head clamp is placed on the patient's head, and this might be done with invasive head posts or by molds of the patient's external contour teeth, etc. The head clamp may actually be the base of a stereotactic arc system, or maybe an arc system itself, but in most surgical operations for neurosurgery a standard head clamp could be used with the addition, as illustrated by this invention, of reference points that are known or predetermined coordinate location on the clamp so as to establish or to correspond to a stereotactic coordinate system associated with the clamp and/or stereotactic arc. Box 906 illustrates the subsequent process of mapping or referencing the reference points on the clamp to the fiducial points, structures, or contours on the patient's anatomy. As shown, this can be done by a variety of different apparatus, means, and methods. For example, as illustrated by the figure just above the box 904, it can be done with a digitized navigator such as the OAS of Radionics, Inc. (which could be substituted by magnetic or infrared tracking systems), or it could be implemented by a stereotactic arc system with arc angles, coordinate slides, etc. that can transfer data from the patient's anatomy and the image scan space to the stereotactic apparatus space. The transfer of the mapping data is illustrated by the line 907 to the computer 903. The computer, by the way, can be a non-graphics computer, but is illustrated here as a computer graphic workstation, possibly associated with the CT or MR scanner itself or as a separate, stand-alone workstation whereby, for example, the referencing or mapping can be done in the operating room at the time of surgery, the image scan data having been transferred or loaded to the computer graphic workstation 903, as illustrated by the lines 910, prior to the surgical episode. The computer of the computer graphic workstation then does the mapping between the image scan coordinate system $P_s$ and the clamp or arc coordinate system $P_c$, and this is illustrated by the box 912. The mapping from the computer is illustrated by the line 914, and any manipulations thereafter could be fed back to the computer for updates or image processing. This might be illustrated as line 914A. Once the mapping is in place, then the correspondence between the frame stereotactic coordinate system and the image scan data coordinate system has been done, and the step, which is one of the objectives of the present invention, of not requiring the placement of head clamp prior to the scan, has been achieved (although, this could be included as part of the claim in this invention and is not intended to be excluded). Thus, one sees by this methodology the possibility of a "frameless" scanning procedure which is followed by placement of a "frame-based" stereotactic clamp or arc system, avoiding the inconvenience of putting the clamp or arc system on the patient while he is awake and in the scanning episode. Thus the scanning can be done days or even weeks prior to the operative procedure without having to place the head clamp or frame on the patient. Also shown are various manipulations that are possible with the computer 903 subsequent to the mapping. For example, box 930 illustrates computation of stereotactic paths or approaches, or paths to the target, of radiation probes therapeutic devices. This could be, for example, arc angle settings for a stereotactic arc system, or couch and gantry settings for a linear accelerator, or projected image directions for an X-ray machine or other imaging device, such as ultrasound. These can all be computed by the computer graphic workstation 903 when the transformation between stereotactic and image data set space has been accomplished. External apparatus, such as treatment machine or arc systems, thus can be registered to the patient's anatomy in the image data space. Box 931 illustrates the computation of multiple targets or target volumes, all in clamp or stereotactic space including settings of arcs that can pass probes to the body. Box 932 illustrates that a wide variety of data manipulations can be implemented on the computer 903. Not just the acquisition of the data, as illustrated by 901, but also manipulation such as reconstructions, slicing, wedging, illustration of safe or non-safe probe paths, indication of pathological or non-pathological target structures including atlases, visualization of slices through a selected or pre-selected or post-selected point after the procedure discussed above, can be rendered on the computer screen so that a selected target by the neurosurgeon or operator can give rise to reconstructed or actual slice views through that target position. Various types of reconstructions such as surface and volume renderings with transparency, color overlays, etc. are all possible and schematically illustrated by the box 932. The box 933 illustrates the use and overlay of therapeutic interventional planning such as radiation planning, radiofrequency planning, and other modalities of treatment which could be used on conjunction with the stereotactic mapping in conjugation with the stereotactic space and external treatment apparatus.

Those skilled in the art can devise variations of the above embodiments and examples which still stay within the scope and intention of the present invention. For example, various types of imaging, fiducial means, reference points, data manipulation, registration apparatus, mapping and transformation apparatus, mathematical, graphical, or non-mathematical and non-graphical reference and mapping techniques, various renderings and computer graphic workstations, various types of mapping schemes to relate the image scan data to stereotactic head clamp or patient attachment devices can be contrived, and other computer graphic image fusion, comparison, manipulation, therapy planning, can all be devised by those skilled in the art and still fall under the teaching and claims of the present invention. The present invention can be used as an intraoperative check, or can be used in conjugation with frame-based stereotaxy to confirm or check the accuracy or consistency of data or clinical practice. For example, the head clamp could be placed on the patient's head invasively or non-invasively at the time of scanning, and still the mapping methods described herein could be applicable, (even though the examples given above, illustrated in the so-called "frameless" mode, where a head clamp or patient attachment means is attached to the patient after the time of scanning). Various types of reference points and reference means can be devised, and variations of the present examples can be considered by those skilled in the art. Divots at given coordinate points on the head clamp, such as element 1 in FIG. 1, can be on the coordinate axes and at discrete numerical positions relative to, for example, the coordinate system $X_c$, $Y_c$, and $Z_c$ in FIG. 1. However, exact numerical placement of such reference points is not necessary. Reference points could be replaced by reference lines which can be aligned by lasers or reference objects which can be observed by cameras and identified so as to make the mapping and registration. A simple example is the use of divots at positions on the head clamp so that the point of a digitizer such as apparatus 20 in FIG. 1 can easily be touched off these points after the head clamp 1 is placed on the patient's anatomy 2. Pins or posts could be used as a substitute for such divots so as to enable easy sterilization, sterile draping, and intraoperative access. The divots could be placed on the base of the stereotactic arc system, or could be other positions on the stereotactic arc system in known, predetermined, or numerically simple positions. As alluded to above, the stereotactic arc itself could be used to give coordinate positions of the fiducial points without the need of touching off specific reference points on the head clamp or stereotactic arc base. This would be another form of mapping, but still fall within the claims of the present invention. The head clamp 1 could be a closed ring of various materials, or it could be open or C-shaped, or it could be merely an attachment or cuff stabilized on the patient's external contour or anatomy. Such transfer methods could be used in a variety of applications going beyond interventive surgery, but merely referencing of the body's position on a table or with respect to other external apparatus, ranging in the fields of cardiology, orthopedics, dentistry, radiation therapy, etc. The apparatus of the present invention could be used in non-clinical applications, where registration of the body orientation would be important.

Having described the invention by the above embodiments, what we claim by U.S. Letters Patent are the following:

1. A method of determining a target position in a patient's anatomy, comprising:
   a. scanning the patient's anatomy with an image scanner to obtain image scan data referenced in an image coordinate reference frame;
   b. identifying physical fiducial points on the patient's anatomy and also identifying corresponding fiducial point images in said image scan data from scanning of the patient's anatomy with said image scanner corresponding to said fiducial points, such that said fiducial points and said fiducial point images index the physical space of the patient's anatomy to said image scanner coordinate reference frame;
   c. applying a patient attachment means to the patient's anatomy, said patient attachment means having a defined stereotactic coordinate system and physical reference points in known coordinate positions with respect to said stereotactic coordinate system;

d. applying registration apparatus adapted to determine physical registration data relating to a relationship between said reference points of said patient attachment means and said fiducial points and which thereby provides a mapping between said image scan data and said stereotactic coordinate system; and e. determining a target position in said stereotactic coordinate system identifiable in said image scan data using said mapping between said image scan data and said stereotactic coordinate system.

2. The method of claim 1 further including the steps of determining a course to said target position based on said image scan data and said mapping.

3. The method of claim 1, wherein said patient attachment means is a surgical head clamp adapted for attachment to the head of the patient's anatomy, and wherein the step of applying includes attaching said surgical head clamp to the head of the patient's anatomy after the step of said scanning of the patient's anatomy with said image scanner.

4. A method of determining a target in a patient's anatomy, comprising:

a. scanning the patient's anatomy using an image scanner to obtain image scan data;

b. identifying fiducial points on the patient's anatomy, the fiducial points being identifiable on images of said patient's anatomy as part of said image scan data from said scanning of said patient's anatomy by said image scanner, such that knowledge of positions of said fiducial points in the patient's anatomy and said images of said patient's anatomy provide indexing of the patient's anatomy to said images of said patient's anatomy;

c. securing a stereotactic patient attachment means to the patient's anatomy, said stereotactic patient attachment means having a stereotactic coordinate system;

d. registering said stereotactic patient attachment means to said fiducial points and thereby registering said patient's anatomy to said patient attachment means and/or said stereotactic coordinate system; and e. determining a target position in said stereotactic coordinate system which is identifiable in said image scan data using said physical reference data.

5. The method of claim 4, further including the step of determining a course to said target position based on said image scan data.

6. A method of registering a stereotactic patient attachment means to a patient's anatomy comprising:

a. scanning the patient's anatomy using an image scanner to obtain image scan data;

b. identifying fiducial points on the patient's anatomy which are identifiable on said image scan data from said scanning of said patient's anatomy with said image scanner, and thereby at known positions with respect to the patient's anatomy;

c. securing stereotactic patient attachment means to the patient's anatomy, said stereotactic patient attachment means having a stereotactic coordinate system and being adapted to provide physical reference data between said stereotactic patient attachment means and said fiducial points so as to register the patient's anatomy with respect to said stereotactic coordinate system;

d. registering said stereotactic patient attachment means to said fiducial points and thereby registering the patient's anatomy and said image scan data with respect to said stereotactic patient attachment means and/or said stereotactic coordinate system.

7. The method of claim 6 further including the step of identifying a target point in said image scan data and registering said target point in said stereotactic coordinate system of said stereotactic patient attachment means.

* * * * *